United States Patent
Lihme et al.

(10) Patent No.: US 6,221,624 B1
(45) Date of Patent: Apr. 24, 2001

(54) PRE-STAINED 3,3',5,5'-TETRAMETHYLBENZIDINE SUBSTRATES FOR THE DETECTION OF ENZYME ACTIVITY

(75) Inventors: Allan Otto Fog Lihme, Birkerød; Margit Wikborg, Copenhagen, both of (DK)

(73) Assignee: Kem-En-Tec A/S, Copenhagen (DK)

( * ) Notice: Subject to any disclaimer, the term of this patent is extended or adjusted under 35 U.S.C. 154(b) by 0 days.

(21) Appl. No.: 09/445,802

(22) PCT Filed: Jul. 15, 1998

(86) PCT No.: PCT/DK98/00333

§ 371 Date: Feb. 9, 2000

§ 102(e) Date: Feb. 9, 2000

(87) PCT Pub. No.: WO99/04261

PCT Pub. Date: Jan. 28, 1999

(30) Foreign Application Priority Data

Jul. 15, 1997 (DK) .................................................. 0870/97

(51) Int. Cl.[7] ............................. C12Q 1/28; C12Q 1/00; G01N 33/53

(52) U.S. Cl. ................................ 435/7.72; 435/28; 435/4; 435/968

(58) Field of Search ................................ 435/7.72, 28, 4, 435/968

(56) References Cited

U.S. PATENT DOCUMENTS

| | | | |
|---|---|---|---|
| 4,128,629 | 12/1978 | Eldred et al. | 424/1 |
| 4,503,143 | 3/1985 | Gerber et al. | 435/28 |
| 4,891,314 | 1/1990 | Pauly, et al. | 435/28 |
| 5,318,894 | 6/1994 | Pugia | 435/28 |

FOREIGN PATENT DOCUMENTS

| | | |
|---|---|---|
| 195 27 160 | 1/1997 | (DE) . |
| 0 279 614 | 2/1988 | (EP) . |
| 0 214 262 | 2/1990 | (EP) . |
| 0 618 300 A1 | 11/1990 | (EP) . |
| WO 85/05688 | 12/1985 | (WO) . |
| 0 456 782 B1 | 11/1990 | (WO) . |
| WO 92/15883 | 9/1992 | (WO) . |
| 99/04261 * | 1/1999 | (WO) . |

OTHER PUBLICATIONS

Database WPI, Section Ch, Week 8936, Derwent Publications Ltd., London, GB; AN 89–259102, XP002081717 & JP 01 187 099 A (Konica Corp), (Jul. 26, 1989).

* cited by examiner

Primary Examiner—Louise N. Leary
(74) Attorney, Agent, or Firm—Foley & Lardner

(57) ABSTRACT

The present invention relates to a method of using a storage-stable, pre-stained 3,3',5,5'-tetramethylbenzidine (TMB) substrate in an enzyme substrate. The TMB substrates comprise: (a) a water-based TMB substrate composition which includes a peroxide, e.g., hydrogen peroxide or urea hydrogen peroxide, and (b) a dye which is soluble therein. Suitable dyes to be included in the substrate preferably have an absorbance at 450 nm of at the most milli absorbance units. Examples of dues are Pholixine B, Eosin B and Quinaldine Red. The substrates are advantageous in that they include a dye which is visible to the human eye. This is especially valuable when the substrates are handled and measured. The substrates are especially suitable for enzyme assays such as enzyme-linked-immunosorbent-assays (ELISA), e.g. horse radish peroxide (HRP) is used. The substrates may advantageously include less than 5% organic solvents and a solubility increasing agent such as polyvinylalcohol. The substrates are storage-stable for more than 12 months.

19 Claims, No Drawings

PRE-STAINED 3,3',5,5'-TETRAMETHYLBENZIDINE SUBSTRATES FOR THE DETECTION OF ENZYME ACTIVITY

FIELD OF THE INVENTION

The present invention relates to 3,3',5,5'-tetramethylbenzidine reagents especially for use in enzyme immunoassay techniques with enzyme labelled antibodies or antigens.

BACKGROUND OF THE INVENTION

Enzyme immunoassay (EIA) is an assay technique based on two facts: (1) the immune system of vertebrates can produce an almost unlimited variety of antibodies each with a specific affinity for an antigen, and (2) the high catalytic power and specificity of enzymes, which it often is quite easy to detect. In the EIA technique, the immuno-reactants, the antibody and the corresponding antigen are reacted with each other and this reaction is detected using enzymes labelled to one of the immuno-reactants. Different enzymes are used in the assay and among these are β-galactosidase, peroxidase, e.g. horseradish peroxidase, and alkaline phosphatase. For the detection of the enzyme activity is used a chromogenic substrate and a chromogen which develop a colour during the reaction. This technique is very useful both for diagnostic purposes and in basic research work. The enzyme immunoassays have several advantages. It is possible to obtain very high sensitivity and specificity with relatively cheap reagents and equipment. The methods to produce monoclonal antibodies have enhanced the possibility of standardisation of EIA with even higher sensitivity and specificity and contributes to new assay designs.

A modification of the EIA and one of the very widely used enzyme immunoassay techniques today is the ELISA (enzyme-linked-immunosorbent-assay) which can be used for both qualitative and quantitative assays. In principle an enzyme is coupled to an antibody against the antigen to be determined. The assay is usually performed in trays of polystyrene or polypropylene to which the antigen is immobilised. The enzyme is chemically coupled to the antibody and incubated with a substrate solution containing a suitable buffer, a chromogenic substrate, e.g. hydrogen peroxide or urea peroxide, and a chromogen which changes colour when the peroxide is oxidised. There are many variations of an ELISA. In competitive assays, the enzyme may be coupled with the antigen. The number of "layers" of antigen and antibodies may vary as well as it is possible to use different enzymes. In ELISA techniques, horseradish peroxidase (HRP) is a commonly used enzyme. For the detection of the enzyme activity is needed a specific enzyme substrate for the actual enzyme. Various enzyme substrates such as ortho-phenylenediamine (OPD), 2,2'-azino-bis-(3-ethylbenz-thiazoline-6-sulfonic acid) (ABTS) and 3,3',5,5'-tetramethylbenzidine (TMB) are commonly used. TMB is a non-hazardous normally colourless substrate, which forms an intensely blue coloured oxidation product in the presence of peroxide and HRP. TMB is often preferred as substrate because it is at this time the most sensitive substrate for HRP and is less toxic than e.g. OPD.

When performing an ELISA assay it is important to reduce the background signal in order to obtain the best possible sensitivity. It has therefore been considered important that the substrate components themselves should be colourless or only very slightly coloured in order for them to be used as substrate in an ELISA assay. Such properties will minimise the blind absorbance values. This means that pipetting of the thus colourless substrate into the enzyme immunoassay reaction vessel, which often is a transparent tube or a transparent ELISA tray, is associated with the risk of incorrect dosage in that it may be difficult to determine immediately by visual examination whether the substrate has been added to a vessel (e.g. a well) or not. As a consequence, the substrate may not be added to all vessels, or twice the required amount of substrate may be added to some vessels. In automated assays it is not easily achievable to make control measurements to ensure that the substrate or the proper amount of substrate has been added.

German Patent No. DE 195 27 160 C1 describes a method for photometrically measuring of the concentration of an enzyme by measuring a colour created by enzymatic reaction with a colourless substrate. The enzymatic reaction is stopped by adding 2 N NaOH. To control the addition of stopping solution a dye (Amaranth) is included in the otherwise colourless solution. The German patent relates to the inclusion of a dye in a stop solution, but does not address the problems of storage stability and construction of water-based substrate systems if a dye should be included in such systems for the same purpose.

U.S. Pat. No. 4,128,629 describes a method for determining small concentrations of cortisol by using an immunoassay technique, more specific a radio-immuno-assay (RIA). In an example the possibility of including a non-interfering red dye to indicate the presence of the tracer used in the assay is mentioned. There is no mentioning of enzyme immunoassays and the specific problems associated to the stabilisation and storage stability of substrate solutions having dyes included therein.

U.S. Pat. No. 5,318,894 describes a dry phase test device and method for determining the presence of a peroxidatively active substance. The test device includes a test pad comprising a suitable carrier matrix with an indicator reagent. The indicator reagent composition for impregnation of the test area of the test device includes an indicator dye (e.g. TMB), a hydroperoxide and a promoter. To improve the colour resolution and differentiation one or more inert background dyes can be included in the indicator reagent. The amount of organic solvent present in the indicator reagent for impregnation is up to 90%. U.S. Pat. No. 5,318,894 does however not address the problems with respect to preparation and storage stability of a water-based TMB substrate solution system. Storage stability of the liquid compositions does not appear to be relevant in that the liquid compositions are used immediately after preparation. Also, the dyes used in U.S. Pat. No. 5,318,894 appears to be selected so that they deliberately have a high absorbance in the same range as the reacted TMB substrate.

DESCRIPTION OF THE INVENTION

The present invention provides a solution to the problems associated with applying an otherwise colourless substrate to a reaction vessel (e.g. manual pipetting of a TMB substrate composition into an ELISA tray) by including a dye in ready-to-use substrates. In this way it has become possible, e.g. to see the substrate both in the pipette and in the reaction vessel, such as an ELISA tray, during pipetting. The dye is so selected that it has substantial no absorbance in the absorbance range under the conditions where the reaction product of the reaction between the substrate and the enzyme is to be detected. Furthermore, the especially selected dyes have substantially no influence on the enzyme-substrate reaction. It has therefore for the first time become possible to provide a substrate which makes manual pipetting easier and more reliable, and thereby also faster without compromising the storage stability of the substrate.

It should be understood that the substrates according to the present invention are equally applicable for automatic pipetting procedures where it is desirable to control (either manually or by automatic means) the addition of a sufficient amount of substrate to the reaction vessel.

Thus generally, the present invention provides a substrate for use in an enzyme immunoassay (where the enzyme immunoassay includes the reaction between an enzyme and an enzyme substrate comprised in the substrate); the substrate comprises a dye which is (a) visible to the human eye when applied to the environment where the enzyme immunoassay is conducted, (b) substantially non-interfering in the reaction between the enzyme substrate and the enzyme, and (c) substantially non-interfering under the conditions used for measuring the reaction product of the reaction between the enzyme substrate and the enzyme.

The substrates described herein may be in the form of a powder, a tablet or a liquid formulation, preferably, the substrates are in the form of a liquid formulation, e.g. a ready-to-use solution, or in the form of a tablet which may easily be dissolved in a suitable medium, e.g. water, a buffer, or a mixture of an organic solvent and water, to provide a solution having the desired concentration.

The substrates may be applicable for any enzyme immunoassays (EIA) known to the person skilled in the art. Of the various EIA techniques available, the ELISA technique is especially interesting since automated set-ups are commercially available. For the HRP-ELISA, suitable enzyme substrates are ortho-phenylenediamine (OPD), 2,2'-azino-bis-(3-ethylbenz-thiazoline-6-sulfonic acid) (ABTS), diaminobenzidine (BAB), and 3,3',5,5'-tetraalkylbenzidine such as 3,3',5,5'-tetramethylbenzidine (TMB), among which 3,3',5,5'-tetramethylbenzidine (TMB) is preferred due to its non-hazardous nature. (it should be understood that the present invention relates to comprising any and all of the above-mentioned enzyme substrates. If alkaline phosphatase is used as enzyme in the EIA substrates, the enzyme substrate may be one of 5-bromo-4-chloro-3-indolyl phosphate (BICP), p-nitrophenyl phosphate (p-NPP), and Fast Red.

In particular, the present invention provides a storage-stable pre-stained 3,3',5,5'-tetramethylbenzidine (TMB) substrate comprising: (a) a water-based TMB substrate composition which includes a peroxide and (b) a dye which is soluble therein.

When used herein, the terms "pre-stained substrate" and "substrates" and similar expressions are intended to mean a substrate composition comprising a dye.

The term "visible to the human eye" is intended to mean that the substrate in question is sufficiently coloured to be identified by the technician in the amounts typically used in enzyme immunoassays. When the substrate is a TMB substrate where the reaction product between TMB, peroxide and HRP is measured at around 450 nm (yellow), it is preferred that the substrate (dye) has a visible colour in the range of 500–600 nm, i.e. in the range clear of the blue and the yellow colours of TMB. It is believed that the absorbance at a wavelength in that range (500–600 nm) should be at least 100 mabs, such as at least 200 mabs, preferably at least 400 mabs.

In order for a dye to be included in a substrate, e.g. in addition to an already established ready-to-use substrate such as a TMB substrate composition, the dye has to fulfil certain criteria.

It is important that the dye is substantially non-interfering in the reaction between the enzyme substrate and the enzyme. Thus, in the case when a horse radish peroxidase-ELISA (HRP-ELISA) is performed, the dye should be substantially non-interfering in the reaction between peroxide, the horseradish peroxidase and TMB as well as substantially non-interfering with the reaction product. It should be understood that a small interference may be acceptable for certain applications, however, in general interference with the reaction may severely compromise the sensitivity of the assay.

As a further criterion, the dye must be completely soluble under the conditions where the reaction product of the enzyme substrate/enzyme reaction is measured. It is believed that dyes having a solubility in the substrate of at least 5 $\mu$g/ml, preferably at least 10 $\mu$g/ml are suitable for the purpose described herein. (When the substrate is presented in the form of a powder or a tablet, the solubility of the dye refers to the final (ready-to-use) concentration.)

A further but not less important criterion (which represents the gist of the present invention) is that the substrate (including the dye) should be visible when it is applied to the reaction vessel where the enzyme immunoassay is conducted, e.g. pipetted into the ELISA tray. However, in connection with this important feature of the dye, it should be substantially non-interfering under the conditions used for measuring the reaction product of the reaction between the enzyme substrate and the enzyme. This should apply even in the case where further reagents (e.g. stop-solutions) are added to the reaction vessel before measurement of the reaction product is performed. In the case where the enzyme immunoassay is based on a HRP/TMB system, the dye should have no influence on the detection of the reaction product, especially not after addition of a stop-solution (e.g. sulphuric acid). Thus, the dye itself should not have any or very little absorbance at the measuring wavelength, often in the range of 400–500 nm or 600–660 nm, in particular at around 450 nm and around 640 nm. For a normal TMB substrate (without dye) the usual blind absorbance values are from 5–20 milli absorbance units (mabs; measured for a volume of 100 $\mu$l in a ELISA tray (diameter 6.7 mm) [this volume to diameter ratio applies generally to the mabs values stated in the description and the claims (unless otherwise stated)]). The dye may cause a small increase, however, the total blind absorbance level should preferably be below 100 mabs, preferably below 75 mabs, such as below 50 mabs at least around 450 nm and around 640 nm, but preferably also in the entire ranges of 400–500 nm and 600–660 nm. Thus, dyes which change from coloured to colourless or colours which have no absorbance at the measuring wavelength under the assay condition can be used.

Since the dye preferably is included in a ready-to-use substrate composition, any (negative) effect on the activity and the long term stability of the substrate, when stored at 4° C. and even at 25° C., should be minimal. The long term stability of the substrate comprising a dye should be as good as for the normal colourless substrate, i.e. often at least 12 months (such as 12–18 months or more) when kept at 4° C. in the dark with less than a 25% decrease in the activity when compared to the initial activity of the substrate. Preferably the reduction of the activity is even less, such as less than 20%, or even less than 10% or less than 5%.

When used herein, the term "TMB substrate composition" is intended to mean an (otherwise substantially colourless) composition which may be used in its own right. Thus, when used herein, a substrate composition may be an already established substrate, however, this should not be construed so that the present invention is limited to inclusion of dyes in presently commercially available TMB substrate compositions.

TMB substrate compositions will typically comprise a number of additives in order to enhance the stability and compatibility with the HRP-ELISA or HRP-EIA. Furthermore, the TMB substrate composition may further comprise the necessary peroxide so that the TMB substrate composition constitutes a "complete" substrate system. A peroxide as a part of the TMB substrate composition is typically selected from hydrogen peroxide and urea hydrogen peroxide, preferably hydrogen peroxide.

From the above it should be understood that the dye should not be a substrate or an inhibitor for horseradish peroxidase (HRP) in the case where the substrate is used in a HRP-ELISA or a HRP-EIA.

In order to avoid hazardous conditions for the technicians working with the substrates, it is especially preferred that the substrates according to the present invention comprises a TMB substrate which includes a water-base solvent system or a solvent system comprising less than 5% (v/v) of organic solvents. In the case where a water-based solvent system is applied (but also in certain cases where an organic solvent system is used) it may be necessary or desirable to include one or more solubility increasing agent(s) in order to facilitate the (permanent) dissolution of the dye. An example of a suitable solubility increasing agent is polyvinyl alcohol, which may already be a constituent of the TMB substrate composition. It is obvious that the relatively low content of organic solvents has been a further challenge towards a solution to the problem solved with the present invention.

Examples of commercially available TMB substrate compositions are: "TMB One Substrate" (ex Kem-En-Tec A/S, Denmark), "TMB PLUS Substrate" (ex Kem-En-Tec A/S, Denmark), "TMB Microwell Peroxidase Substrate" (ex Kirkegaard & Perry Laboratories), "K-Blue" (ex ElisaTechnologies) and "TMB Peroxidase Substrate" (ex MOSS Inc.).

For substrates for other enzyme immunoassays similar principles apply mutatis mutandis.

In the present context the term "dye" is intended to have its normal meaning, namely a "soluble" colorant. Dyes which have suitable properties with respect to at least some of the above-mentioned parameters are, e.g., Phloxine B, Eosin B, and Quinaldine Red, Naphthol Yellow, Basic Fuchsin, m-Cresol Purple, Thymol Blue, Xylenol Blue, Nile Blue A, Thymolphthalein, among which Phloxine B seems to be the most suitable.

A preferred embodiment of the present invention, relates to a substrate comprising 3,3',5,5'-tetramethylbenzidine (TMB), Phloxine B, hydrogen peroxide, one or more additives including any solubility increasing agent(s), and a water-based solvent system.

The present invention also relates to the use of the substrates described herein in an enzyme immunoassay, such as an ELISA.

Furthermore, the present invention also relates to the use of a dye for the preparation of substrate for an enzyme immunoassay, such as an ELISA, where said dye is present in the substrate in such a concentration that the dye is visible to the human eye. Especially interesting dyes for that purpose are Phloxine B, Eosin B, and Quinaldine Red.

EXAMPLES

General Procedure for ELISA Assay Using TMB Substrates

In all of the following examples, the following ELISA procedure has been used. The assay is a three layer sandwich ELISA. For all three layers are used Rabbit Anti-Human IgG, Human Serum Protein Calibrator, and Rabbit Anti-Human IgG-HRP from Dako A/S, Denmark. The plate is coated with the first antibody to which the antigen is coupled as the second layer. This layer is usually the sample to be analysed but since our aim is to analyse the substrate the "sample" is the same antigen in all assays. To this antigen is coupled a second antibody-enzyme conjugate. The assay is in the following described in details.

The assay is performed in Polystyrene MAXISorp plates (flat bottomed wells) from Nalge NUNC International.

First layer: Rabbit Anti-Human IgG (DAKO A 0423); is diluted 1:1000 in 0.1 M $KH_2PO_4$, pH 7.2, 100 $\mu$l is added to each well and incubates overnight at 4° C. The antibody is decanted and the wells are washed once with washing buffer (0.1 M $KH_2PO_4$; 0.5 M NaCl; 0.1% Tween 20; pH 7.2). 200 $\mu$l blocking solution (0.1 M $KH_2PO_4$; 0.5% Tween 20; pH 7.2) is added and incubates 30 minutes at room temperature. The blocking solution is decanted and the wells washed twice with washing buffer.

Second layer: Human Serum Protein Calibrator (DAKO X 0908) is diluted to 4 ng/ml in 0.1 M $KH_2PO_4$, pH 7.2, 100 $\mu$l is added to each well and incubates overnight at room temperature. The antigen dilution is decanted and the wells washed three times in washing buffer.

Third layer: Rabbit anti Human IgG-HRP (DAKO P 214) is diluted 1:1000 in 0.1 M $KH_2PO_4$, pH 7.2, 100 $\mu$l is added and incubates 2 hours at room temperature. The antibody enzyme-conjugate is decanted and the wells washed three times in washing buffer.

The plate is then ready for addition of the TMB substrate to be tested. For each substrate to be tested is used one column (=eight wells). This means that each substrate is analysed in an eight fold determination. 100 $\mu$l substrate is added and incubates for 13 minutes at room temperature. The reaction is stopped by adding 100 $\mu$l 0.2 M sulphuric acid and the plate is read in an ELISA (BIO-TEK Instruments EL 312e) at 450 nm with 630 nm as reference wavelength. When running an assay a stable TMB Substrate, TMB Microwell Peroxidase Substrate from Kirkegaard & Perry Laboratories, is included as standard in one column in every tray. The activity of the tested substrate is the mean of eight determinations and is compared to this standard.

The blind absorbance value of the substrate is determined by adding 100 $\mu$l substrate to a column of an uncoated ELISA plate adding 100 $\mu$l 0.2 M sulphuric acid and reading the plate at 450 nm with 630 nm as reference wavelength. The blind absorbance value is the mean value of eight determinations.

Example 1

Addition of Dye to TMB Substrates

Phloxine B (Sigma) is a dye which is red to purple at the pH of the substrate and change to colourless by addition of sulphuric acid. Phloxine B was added to 5 different ready-to-use substrates: TMB One Substrate; Kem-En-Tec A/S, TMB PLUS Substrate; Kem-En-Tec A/S, TMB Microwell Peroxidase Substrate; Kirkegaard & Perry Laboratories (TMB 1), K-Blue; ElisaTechnologies (TMB 2) and TMB Peroxidase Substrate; MOSS Inc. (TMB 3) The concentration of the dye was 15 $\mu$g per ml of substrate. The pre-stained substrates were visually examined for precipitation of the dye and graduated from "+++" (heavy precipitation) to "−" (no precipitation). Furthermore, the blind value of the substrates was read at 450 nm with 630 nm as reference wavelength in an ELISA-tray, see general procedure above. The results are shown in Table 1.

TABLE 1

| Substrate | Precipitation | Blind value Pre-stained (mabs) | Blind value Reference (mabs) |
|---|---|---|---|
| TMB One | – | 27 | 9 |
| TMB Plus | +++ | — | 8 |
| TMB 1 | – | 102 | 9 |
| TMB 2 | +++ | — | 47 |
| TMB 3 | – | 74 | 9 |

For two of the substrates, TMB Plus and TMB 2, the addition of dye caused heavy precipitation when the dye was added to the ready-to-use substrates. There was no precipitation in three of the remaining dyed substrates. One of them (TMB One) will be usable in an ELISA because the blind value is lower than the desired 50–75 mabs. For the other two substrates (TMB 1 and TMB 3), the addition of the dye caused an increase in the blind value to a level higher than or very close to 75 mabs.

Example 2

Improving the Solubility of the Dye

To improve the solubility, polyvinyl alcohol, which is one of the components already present in some of the substrate compositions, was added. Polyvinyl alcohol (PVA) is present in the two Kem-En-Tec substrate compositions (TMB One and TMB Plus) and the amount was increased by adding 0.100 mg/ml and 0.152 mg/ml respectively to a final concentration of 0.200 mg/ml. To the other three tested substrates was added 0.200 mg PVA/ml to a concentration of at least 0.200 mg/ml. Subsequently, Phloxine B was added in the same concentration as in Example 1, i.e. 15 μg/ml.

The pre-stained substrates were again visually examined for precipitation of the dye and the blind value of the substrates was read at 450/630 nm in an ELISA-tray (see the general procedure above). The results are shown in Table 2.

TABLE 2

| Substrate | Precipitation | Blind value Pre-stained (mabs) | Blind value Reference (mabs) |
|---|---|---|---|
| TMB One | – | 24 | 9 |
| TMB Plus | – | 17 | 8 |
| TMB 1 | + | — | 9 |
| TMB 2 | ++ | — | 47 |
| TMB 3 | – | 67 | 9 |

TMB One and TMB Plus both had good visibility after pipetting in the ELISA tray and acceptable blind values well below 50 mabs.

Example 3

Determination of the Optimal Concentration of the Dye

To the TMB Standard and TMB Plus substrates were added extra polyvinylalcohol as in example 2 and Phloxine B was added in the concentrations stated in Table 3.

TABLE 3

| | 2 μg/ml | | 10 μg/ml | | 50 μg/ml | |
|---|---|---|---|---|---|---|
| Substrate | Precip. | Blind | Precip. | Blind | Precip. | Blind |
| TMB One pre-stained | – | 23 | – | 29 | + | — |
| TMB Plus pre-stained | – | 18 | – | 21 | – | 30 |

The optimal concentration of dye is a combination of its solubility in the substrate formulation, the increase in the blind value and the colour must be strong enough to be visible in the ELISA tray. With a concentration of 2 μg/ml the substrates are almost colourless. A concentration of 10 μg/ml gives good visibility and an acceptable blind value. The high concentration of 50 μg/ml leads to precipitation of dye in the TMB One substrate. In the TMB Plus substrate composition the blind value is below 50 mabs. Since the visibility is good at both 10 and 50 μg/ml, it is p referred to add only the necessary amount of the dye and a concentration of 10 μg/ml thus seems to be sufficient.

Example 4

A Dyed TMB Substrate vs. a "Normal" TMB Substrate

The activity of TMB One substrate and TMB Plus substrate was compared to the activity when extra PVA and a dye was added to the formulation. Extra PVA was added as in example 2. The dye Phloxine B was used in a concentration of 10 μg/ml.

TABLE 4

| Substrate | Blind (mabs) | Activity (mabs) |
|---|---|---|
| TMB One | 12 | 950 |
| TMB One Pre-stained | 25 | 977 |
| TMB Plus | 19 | 1164 |
| TMB Plus Pre-stained | 32 | 1193 |

These results show that the addition of a dye to the two TMB formulations has very little influence on the blind absorbance value and the activity is the same for both substrates.

Example 5

Test of Various Dyes

Three different dyes Phloxine B, Eosin B and Quinaldine Red all from Sigma Chemical Co. were tested for their performance when included in the formulation of TMB Plus substrate in a concentration of 10 μg/ml together with polyvinylalcohol (0.152 mg/ml–total amount 0.200 mg/ml). The performance was tested as described in the general procedure. The results are shown in Table 5.

TABLE 5

| Dye | Blind (mabs) | Activity (mabs) |
|---|---|---|
| No dye (reference) | 9 | 1083 |
| Phloxine B | 15 | 1063 |
| Eosin B | 17 | 999 |
| Quinaldine Red | 17 | 843 |

None of the dyes precipitated at a concentration of 10 μg/ml. The blind value is good for all the selected dyes, but the activity is slightly affected by Eosin B and Quinaldine Red. The decrease in activity for Eosin B is about 8% and could be acceptable but for Quinaldine Red the decrease is about 25% which for some practical uses may be unacceptable. In certain cases it may, however, not be a prohibitive effect for the use of the substrate and should therefore be regarded as being within the scope of the present invention.

Example 6

Long Term Stability of Pre-stained Substrates

To examine the long term stability of the pre-stained TMB Standard and TMB Plus substrate, small bottles (Nalgene amber 15 ml bottles) containing freshly produces substrate were placed at 4° C. and 20° C. in the dark. From time to time bottles of substrate were analysed in the assay described in the general procedure. The activity of the substrate was set to 100% at the day of production. The results of the stability tests are shown in the tables below.

TABLE 6

| TMB One | Blind absorbance mabs | | Activity % | |
| --- | --- | --- | --- | --- |
| Substrate | 4° C. | 20° C. | 4° C. | 20° C. |
| Day 1 | 19 (8)* | 19 (8)* | 100 (100)* | 100 (100)* |
| Day 84 | 30 (13)* | 29 (12)* | 98 (100)* | 99 (100)* |
| Day 345 | 30 (19)* | 33 (18)* | 100 (100)* | 74 (77)* |

*( ) Reference value for unstained substrate

TABLE 7

| TMB One | Blind absorbance mabs | | Activity % | |
| --- | --- | --- | --- | --- |
| Substrate | 4° C. | 20° C. | 4° C. | 20° C. |
| Day 1 | 25 (8)* | 25 (8)* | 100 (100)* | 100 (100)* |
| Day 105 | 23 (7)* | 26 (7)* | 98 (100)* | 64 (78)* |
| Day 366 | 19 (9)* | 40 (21)* | 96 (100)* | 33 (44)* |

*( ) Reference value for unstained substrate

As seen from the tables both substrates have very good long term stability, very similar tot he un-stained commercial substrates. After almost a year at 4° C. the TMB Standard substrate did not lose any activity and there was no increase in the blind absorbance. At 20° C. there was loss in activity of about 25% which is generally expected for a substrate after storing at ambient temperature for that long time. For the TMB Plus substrate there was no increase in the blind absorbance and very little decrease in activity at 4° C. (virtually insignificant). After around one year at 20° C. there was some loss in activity. It was expected observe a higher loss at 20° C. for this substrate due to the higher activity level.

What is claimed is:

1. A method of using a storage-stable, pre-stained 3,3',5,5'-tetramethylbenzidine (TMB) substrate in an enzyme immunoassay, where the enzyme immunoassay includes the reaction between an enzyme and TMB; said substrate comprising a water based TMB substrate composition which includes a peroxide and a dye, said dye being (a) visible to the human eye when applied to the reaction vessel wherein the enzyme immunoassay is conducted, (b) substantially non-interfering in the reaction between TMB and the enzyme, (c) substantially non-interfering under the conditions used for measuring the reaction product of the reaction between TMB and the enzyme, and (d) completely soluble in the substrate under the conditions where the reaction product of TMB and the enzyme is measured.

2. The method according to claim 1, wherein the activity of the substrate decreases with less than 25% compared with the initial activity when the substrate is stored in the dark for a period of a least 12 months at 4° C.

3. The method according to claim 2, wherein the decrease in activity is less than 20%.

4. The method according to claim 1, wherein the peroxide is selected from hydrogen peroxide and urea hydrogen peroxide, preferable hydrogen peroxide.

5. The method according to claim 1, wherein the substrate comprises less than 5% (v/v) of organic solvents.

6. The method according to claim 1, wherein the solubility of the dye in the TMB substrate composition is at least 10 $\mu$g/ml.

7. The method according to claim 1, wherein the pre-stained TMB substrate has an absorbance at 450 nm of at the most 100 milli absorbance units (mabs).

8. The method according to claim 1, wherein the pre-stained TMB substrate has an absorbance in the entire range of 400–500 nm of at the most 75 milli absorbance units (mabs).

9. The method according to claim 1, wherein the pre-stained TMB substrate has an absorbance at 640 nm of at the most 100 milli absorbance units (mabs).

10. The method according to claim 1, wherein the pre-stained TMB substrate has an absorbance in the entire range of 600–660 nm of at the most 75 milli absorbance units (mabs).

11. The method according to claim 1, wherein the pre-stained TMB substrate has an absorbance at a wavelength in the range of 500–600 nm of a least 100 milli absorbance units (mabs).

12. The method according to claim 1, wherein the dye is not a substrate or an inhibitor for horse-radish peroxidase (HRP).

13. The method according to claim 1, wherein the dye is not affecting the reaction or the reaction product from the reaction between 3,3',5,5'-tetramethylbenzidine (TMB), horse-radish peroxidase (HRP), and a peroxide.

14. The method according to claim 1, wherein the dye is selected from Phloxine B, Eosin G, and Quinaldine Red.

15. The method according to claim 14, wherein the dye is Phloxine B.

16. The method according to claim 1, wherein the substrate further comprising one or more solubility increasing agent(s).

17. The method according to claim 16, wherein the solubility increasing agent is polyvinylalcohol.

18. The method according to claim 1, wherein the substrate comprises 3,3',5,5'-tetramethylbenzidine (TMB), Phloxine B, hydrogen peroxide, one or more additives, and a water-based solvent system.

19. The method according to claim 1, wherein the enzyme immunoassay is an ELISA.

* * * * *